US009918615B2

(12) United States Patent
Hamazaki

(10) Patent No.: US 9,918,615 B2
(45) Date of Patent: Mar. 20, 2018

(54) ENDOSCOPE BUTTON UNIT AND ENDOSCOPE

(71) Applicant: OLYMPUS CORPORATION, Tokyo (JP)

(72) Inventor: Masanori Hamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/193,175

(22) Filed: Jun. 27, 2016

(65) Prior Publication Data

US 2016/0302646 A1    Oct. 20, 2016

Related U.S. Application Data

(63) Continuation of application No. PCT/JP2015/057455, filed on Mar. 13, 2015.

(30) Foreign Application Priority Data

Apr. 24, 2014  (JP) .................................. 2014-090454

(51) Int. Cl.
*A61B 1/12* (2006.01)
*A61B 1/00* (2006.01)
(Continued)

(52) U.S. Cl.
CPC ............ *A61B 1/00068* (2013.01); *A61B 1/00* (2013.01); *A61B 1/015* (2013.01); *G02B 23/24* (2013.01);
(Continued)

(58) Field of Classification Search
CPC . A61B 1/00064; A61B 1/00066; A61B 1/015; A61B 1/121; A61B 1/123;
(Continued)

(56) References Cited

U.S. PATENT DOCUMENTS

| 5,104,379 A | 4/1992 | Nakamura et al. |
| 5,299,561 A | 4/1994 | Yoshimoto |

FOREIGN PATENT DOCUMENTS

| JP | H2-63801 U | 5/1990 |
| JP | H03-047275 A | 2/1991 |

(Continued)

OTHER PUBLICATIONS

International Search Report dated Jun. 9, 2015 issued in PCT/JP2015/057455.

(Continued)

*Primary Examiner* — Ryan Henderson
*Assistant Examiner* — Pamela F Wu
(74) *Attorney, Agent, or Firm* — Scully, Scott, Murphy & Presser, P.C.

(57) ABSTRACT

An endoscope button unit includes a housing having two housing portions, a claw portion that is capable of being locked to a cylinder, and is provided at the housing portion, a connection portion that connects the two housing portions, a ring-shaped portion that is placed at an upper portion of the housing portion and is capable of being pulled with use of a finger or a jig, and a connection portion that connects the housing portion and the ring-shaped portion.

12 Claims, 14 Drawing Sheets

(51) Int. Cl.
  *G02B 23/24* (2006.01)
  *A61B 1/015* (2006.01)
(52) U.S. Cl.
  CPC ...... *G02B 23/2476* (2013.01); *A61B 1/00064* (2013.01); *A61B 1/00066* (2013.01)
(58) Field of Classification Search
  CPC ......... A61B 1/125; A61B 1/126; A61B 1/127; A61B 1/12; A61B 1/00068
  USPC .................. 600/121–125, 133, 156–159
  See application file for complete search history.

(56) References Cited

FOREIGN PATENT DOCUMENTS

| JP | H05-049596 A | | 3/1993 |
|---|---|---|---|
| JP | H06-343605 A | | 12/1994 |
| JP | 2002-282205 A | | 10/2002 |
| JP | 2006-167065 A | | 6/2006 |
| JP | 2006-175175 A | | 7/2006 |
| JP | 2006-212048 A | | 8/2006 |
| JP | 2006212048 A | * | 8/2006 |
| JP | 2013-183935 A | | 9/2013 |

OTHER PUBLICATIONS

Japanese Office Action dated Dec. 15, 2015 issued in JP 2015-543979.

* cited by examiner

ENDOSCOPE BUTTON UNIT AND ENDOSCOPE

CROSS REFERENCE TO RELATED APPLICATION

This application is a continuation application of PCT/JP2015/057455 filed on Mar. 13, 2015 and claims benefit of Japanese Application No. 2014-090454 filed in Japan on Apr. 24, 2014, the entire contents of which are incorporated herein by this reference.

BACKGROUND OF THE INVENTION

1. Field of the Invention

The present invention relates to an endoscope button unit and an endoscope.

2. Description of Related Art

Conventionally, endoscopes have been widely used in a medical field and an industrial field. In the medical field, endoscopes are cleaned and disinfected by cleaning/disinfecting apparatuses after use.

When an endoscope is cleaned and disinfected by a cleaning/disinfecting apparatus, a valve unit provided in an operation portion or the like is detached, and is discarded or cleaned and disinfected. The endoscope is provided with various buttons such as an air/water feeding button and a suction button which an inspector operates, and the buttons and the valve units are detached from the endoscope.

When the valve units are detached from the endoscope, it cannot be sometimes judged whether the valve units are already used, or unused by an appearance, and therefore management of used valve units and unused valve units is important.

Consequently, there are proposed such a valve unit that when the suction valve unit including a suction button is detached, a part of the valve unit is deformed and the valve unit can be confirmed to be already used at a glance, and a valve unit that is made incapable of being fitted to an endoscope again, as in the disclosures of Japanese Patent Application Laid-Open Publication No. 2006-175175 and Japanese Patent Application Laid-Open Publication No. 2013-183935.

For example, in the suction valve unit, a part of the attachment portion to be attached to a cylinder which is provided in the operation portion of an endoscope has a deformable or a breakable configuration. The attachment portion is pinched with fingers and the attachment portion is torn off, whereby the part of the attachment portion is deformed or broken, and the suction valve unit can be detached from the operation portion.

SUMMARY OF THE INVENTION

An endoscope button unit of one aspect of the present invention includes a first piston capable of being fitted to a first cylinder of an endoscope, a first housing portion configured to hold the first piston so that the first piston is capable of advancing and retreating along an axial direction of the first piston, a locking portion that is capable of locking the first housing portion to the first cylinder, and is provided at the first housing portion, a second piston capable of being fitted to a second cylinder adjacent to the first cylinder of the endoscope, a second housing portion configured to hold the second piston so that the second piston is capable of advancing and retreating along an axial direction of the second piston, a housing connection portion configured to connect the first housing portion and the second housing portion, a hook portion that is placed at an upper portion of the first housing and is capable of being pulled, a hook connection portion that is disposed at an opposite side with respect to the second housing portion, in the first housing portion, with an axis of the first piston between the second housing and the hook connection portion, and is configured to connect the first housing portion and the hook portion, and a cutout portion that is provided in a portion facing the first housing portion, in the second housing portion.

An endoscope of one aspect of the present invention has the endoscope button unit of the present invention.

DETAILED DESCRIPTION OF PREFERRED EMBODIMENTS

Hereinafter, embodiments of the present invention will be described with reference to the drawings.

First Embodiment (Configuration of Endoscope)

Figure 1:
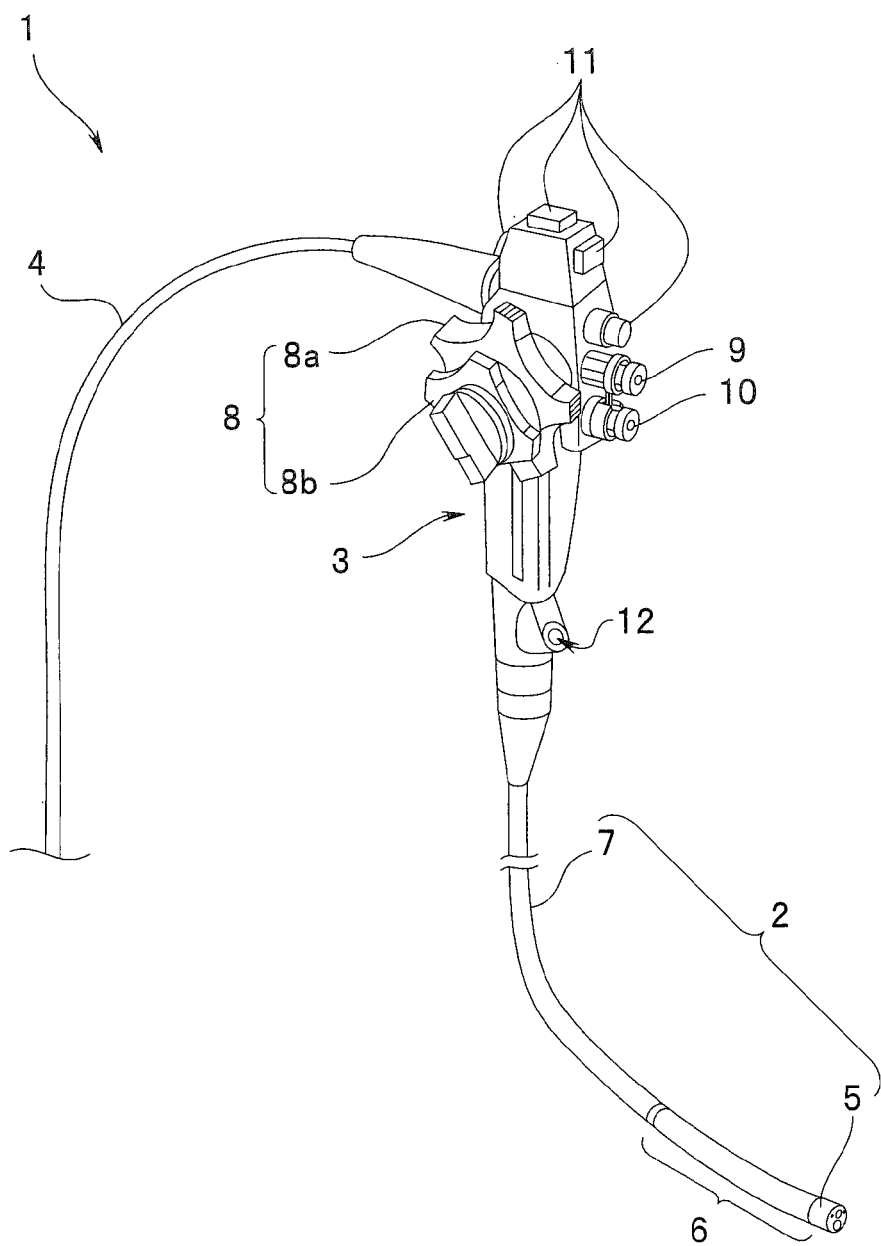
FIG. 1 is an external view showing a configuration of an endoscope according to a first embodiment of the present invention.

FIG. 1 is an external view showing a configuration of an endoscope according to the present embodiment. An endoscope 1 shown in FIG. 1 is configured by including an insertion portion 2 which is long and elongated, an operation portion 3 and a universal cable 4 which is an electric cable.

The insertion portion 2 of the endoscope 1 is configured by a distal end portion 5, a bending portion 6 and a flexible tube portion 7 being provided continuously in sequence from a distal end. The operation portion 3 is provided at a proximal end side of the flexible tube portion 7 which configures the insertion portion 2. The operation portion 3 is provided with a bending operation knob portion 8 for performing a bending operation of the bending portion 6 of the insertion portion 2, a button 9 for air/water feeding, a button 10 for suction, switches 11 of various endoscope functions and the like. The bending operation knob portion 8 is formed of a vertical bending operation knob 8a for performing a bending operation of the bending portion 6 in a vertical direction, and a lateral bending operation knob 8b for performing a bending operation of the bending portion 6 in a lateral direction.

At a distal end side of the operation portion 3, an opening 12 that communicates with a treatment instrument insertion channel is provided. Various treatment instruments are inserted through the treatment instrument channel from the opening 12.

The universal cable 4 which is extended from the operation portion 3 has an endoscope connector (not illustrated) which is attachable to and detachable from a light source apparatus, at an end portion of the universal cable 4. Though not illustrated, one end of a video cable is detachably connected to the endoscope connector, and the other end of the video cable is connected to a video processor.

Figure 2:
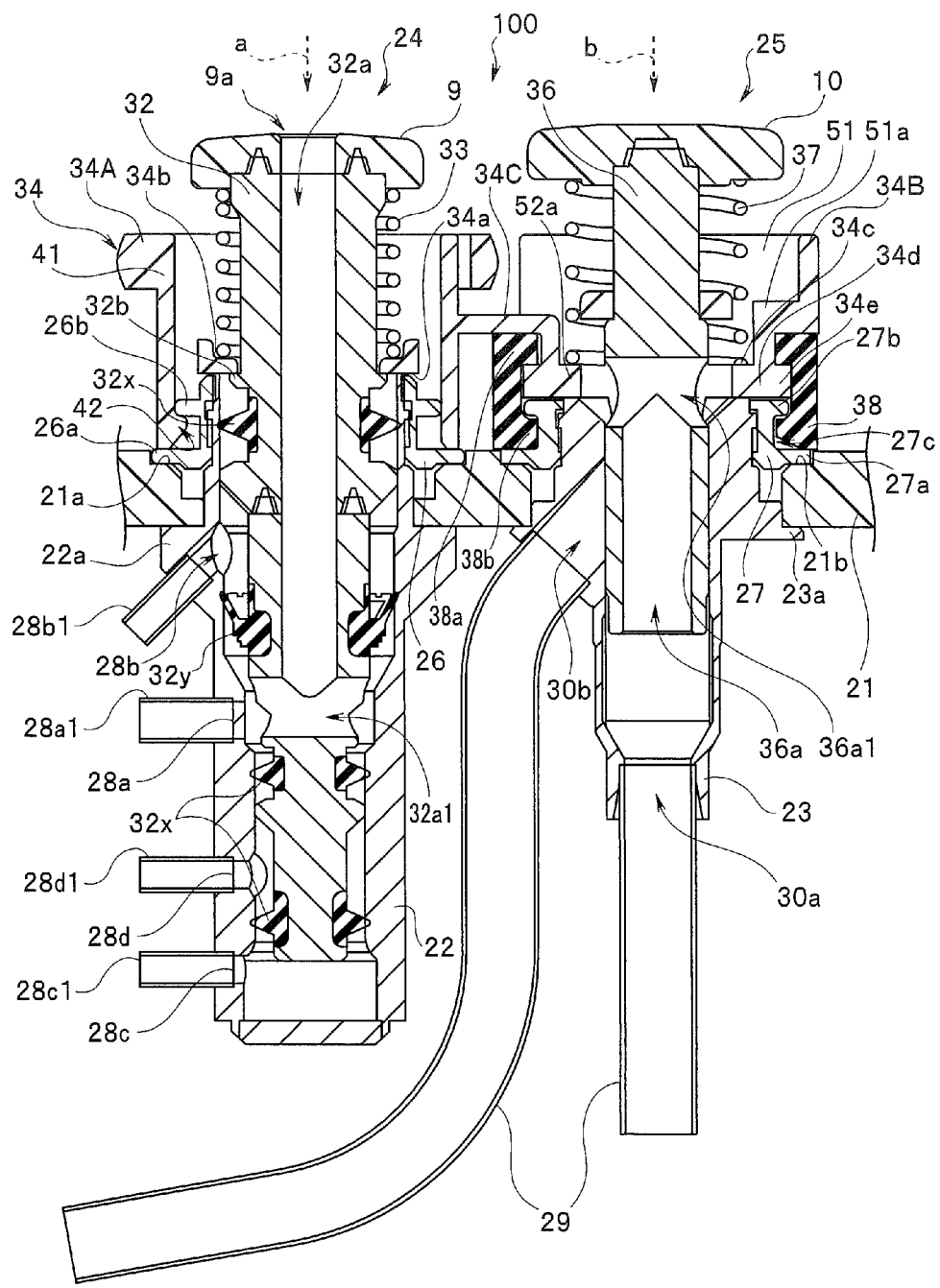
FIG. 2 is a sectional view of an endoscope button unit which is fitted to an air/water feeding cylinder 22 and a suction cylinder 23 that are fixed to an outer sheath member of an operation portion 3, according to the first embodiment of the present invention.
Figure 3:
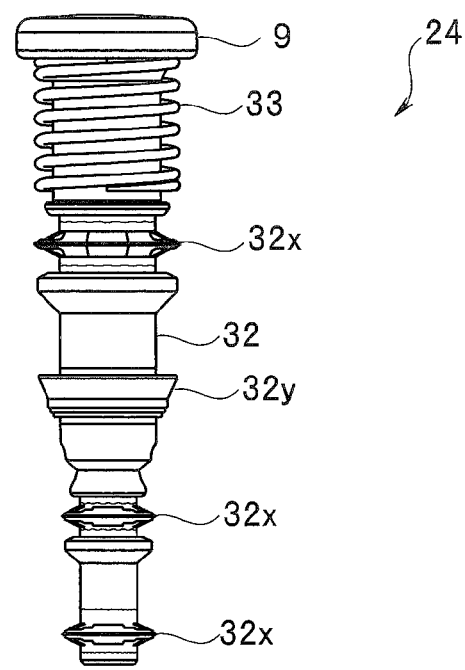
FIG. 3 is a front view of an air/water feeding valve unit 24 according to the first embodiment of the present invention.
Figure 4:
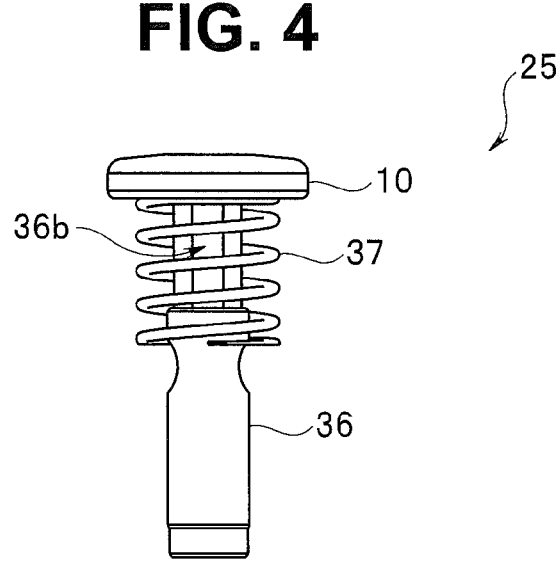
FIG. 4 is a front view of a suction valve unit 25 according to the first embodiment of the present invention.

FIG. 2 is a sectional view of an endoscope button unit 100 that is fitted to the air/water feeding cylinder 22 and the suction cylinder 23 which are fixed to an outer sheath member of the operation portion 3. FIG. 3 is a front view of the air/water feeding valve unit 24. FIG. 4 is a front view of a suction valve unit 25.

The air/water feeding cylinder 22 and the suction cylinder 23 are fixed to an outer sheath member 21 of the operation portion 3.

The air/water feeding cylinder 22 has a shape of a bottomed cylinder with one end opened and the other end closed. A metallic pipe sleeve 26 formed from stainless steel or the like is made detachably fixable to an upper end portion of the air/water feeding cylinder 22 by screwing with a screw, for example. An outward flange portion 26a is formed at a lower end side of the pipe sleeve 26, and an outward flange portion 26b is formed at an upper end side of the pipe sleeve 26.

The air/water feeding cylinder 22 has an outward flange portion 22a midway in a longitudinal direction. When the pipe sleeve 26 is screwed onto the air/water feeding cylinder 22, the air/water feeding cylinder 22 is fixed to the outer sheath member 21 in such a manner that the outer sheath member 21 is sandwiched by the outward flange portion 22a and the outward flange portion 26a.

The suction cylinder 23 has a cylindrical shape. A metallic pipe sleeve 27 formed from stainless steel or the like is made detachably fixable to an upper end portion of the suction cylinder 23 by screwing with a screw, for example. An outward flange portion 27a is formed at a lower end side of the pipe sleeve 27, and an outward flange portion 27b is formed at an upper end side of the pipe sleeve 27.

The suction cylinder 23 has an outward flange portion 23a midway in a longitudinal direction. When the pipe sleeve 27 is screwed onto the suction cylinder 23, the suction cylinder 23 is fixed to the outer sheath member 21 in such a manner that the outer sheath member 21 is sandwiched by the outward flange portion 23a and the outward flange portion 27a.

The air/water feeding cylinder 22 has four of openings 28a and 28b, an opening 28c and an opening 28d. As shown in FIG. 2, a first opening 28a and a second opening 28b are formed in a side wall at an opening side of the air/water feeding cylinder 22. A third opening 28c and a fourth opening 28d are formed in a side wall at a bottom portion side of the air/water feeding cylinder 22. The first opening 28a, the second opening 28b, the third opening 28c and the fourth opening 28d are respectively provided with connection portions 28a1, 28b1, 28c1 and 28d1. Air feeding conduits are connected to the connection portions 28a1 and 28b1, and water feeding conduits are connected to the connection portions 28c1 and 28d1.

The first opening 28a is an air feeding conduit side fluid introduction port that is an opening at an upstream side which is connected to an air feeding apparatus to have gas introduced to the opening. The second opening 28b is an air feeding conduit side fluid lead-out port which is an opening at a downstream side from which gas is led out. The third opening 28c is a water feeding conduit side fluid introduction port that is an opening at an upstream side which is connected to a water feeding apparatus to have a liquid introduced to the opening. The fourth opening 28d is a water feeding conduit side fluid lead-out port which is an opening at a downstream side from which a liquid is led out.

The suction cylinder 23 is disposed midway in a suction channel 29 which is a suction conduit. In the suction cylinder 23, two openings 30a and 30b which communicate with the suction channel 29 are formed.

The air/water feeding valve unit 24 includes a button 9, a piston 32 and a spring 33. The air/water feeding valve unit 24 is mounted on a housing 34.

That is, the piston 32 is fittable to the air/water feeding cylinder 22, and a first housing portion 34A of the housing 34 holds the piston 32 so that the piston 32 is capable of advancing and retreating along an axial direction of the piston 32.

The button 9 has a hole 9a that communicates with a vertical bore 32a which is formed in the piston 32.

In the piston 32, a communication hole 32a1 that communicates with a lower end of the vertical bore 32a and is formed in a direction orthogonal to an axis of the vertical bore 32a is formed. At an outer circumferential portion of the piston 32, rubber ring-shaped seal members 32x at three spots and a ring-shaped check valve 32y are provided.

The piston 32 is passed through the spring 33. The spring 33 is provided in a compressed state between a spring reception portion 34b which is provided in the housing 34, and the button 9, with an outward flange portion 32*b* provided at the piston 32 butted to a bottom surface portion 34*a* of the housing 34.

A configuration of the housing 34 will be described later.

When the button 9 is pressed down against a force of the spring 33, the piston 32 moves in the air/water feeding cylinder 22 in a direction shown by an arrow a of a dotted line.

Thereby, a surgeon can perform air feeding from a nozzle which is provided at a distal end portion of the insertion portion 2, by closing, with a finger, the hole 9*a* of the button 9 for air/water feeding of the air/water feeding valve unit 24 which is fitted to the air/water feeding cylinder 22. Further, the surgeon presses down the button 9 for air/water feeding, whereby the piston 32 moves in the air/water feeding cylinder 22, and the surgeon can performs water feeding from the nozzle which is provided at the distal end portion of the insertion portion 2.

The suction valve unit 25 includes a button 10, a piston 36 and a spring 37. The suction valve unit 25 is mounted on the housing 34.

That is, the piston 36 is fittable into the suction cylinder 23 which is adjacent to the air/water feeding cylinder 22, and a second housing portion 34B of the housing 34 holds the piston 36 so that the piston 36 is capable of advancing and retreating along an axial direction of the piston 36.

The button 10 is fixed to an upper end of the piston 36. A vertical bore 36*a* is formed in a lower side of the piston 36. In the piston 36, a communication hole 36*a*1 that communicates with an upper end of the vertical bore 36*a* and is formed in a direction orthogonal to an axis of the vertical bore 36*a* is formed.

Further, two groove-shaped concave portions 36*b* along the axial direction are formed on an upper portion of an outer circumferential face of the piston 36.

The piston 36 is passed through a spring 37. The spring 37 is provided in a compressed state between a spring reception portion 34*c* that is provided in the second housing portion 34B of the housing 34 and the button 10.

The housing portion 34B has a ring-shaped bottom portion 34*d* which is in close contact with the pipe sleeve 27. The bottom portion 34*d* has an outward flange portion 34*e*, and an elastic member 38 which covers the outward flange portion 34*e* is fitted to the bottom portion 34*d*.

The elastic member 38 has a shape that covers the bottom portion 34*d* and the outward flange portion 27*b* in a state where a bottom face of the bottom portion 34*d* and a top face of the outward flange portion 27*b* of the pipe sleeve 27 are in close contact with each other. Since the housing portion 34B is fitted to the suction cylinder 23 by the elastic member 38, the housing portion 34B is stably fitted to the suction cylinder 23. That is, the elastic member 38 has an effect of stabilizing a fitting state of the housing portion 34B.

A configuration of the elastic member 38 will be described later.

When the button 10 is pressed down against the force of the spring 37, the piston 36 moves in the suction cylinder 23 in a direction shown by an arrow b of a dotted line.

Thereby, the button 10 of the suction valve unit 25 which is fitted to the suction cylinder 23 is pressed down, whereby the piston 36 moves inside the suction cylinder 23, and suction from a suction port that is provided at the distal end portion of the insertion portion 2 can be performed.

Since flows of gas and the liquid in the cylinders at a time of the pistons 32 and 36 moving are known to the public, explanation will be omitted.

(Configuration of Endoscope Button Unit)

Figure 5:
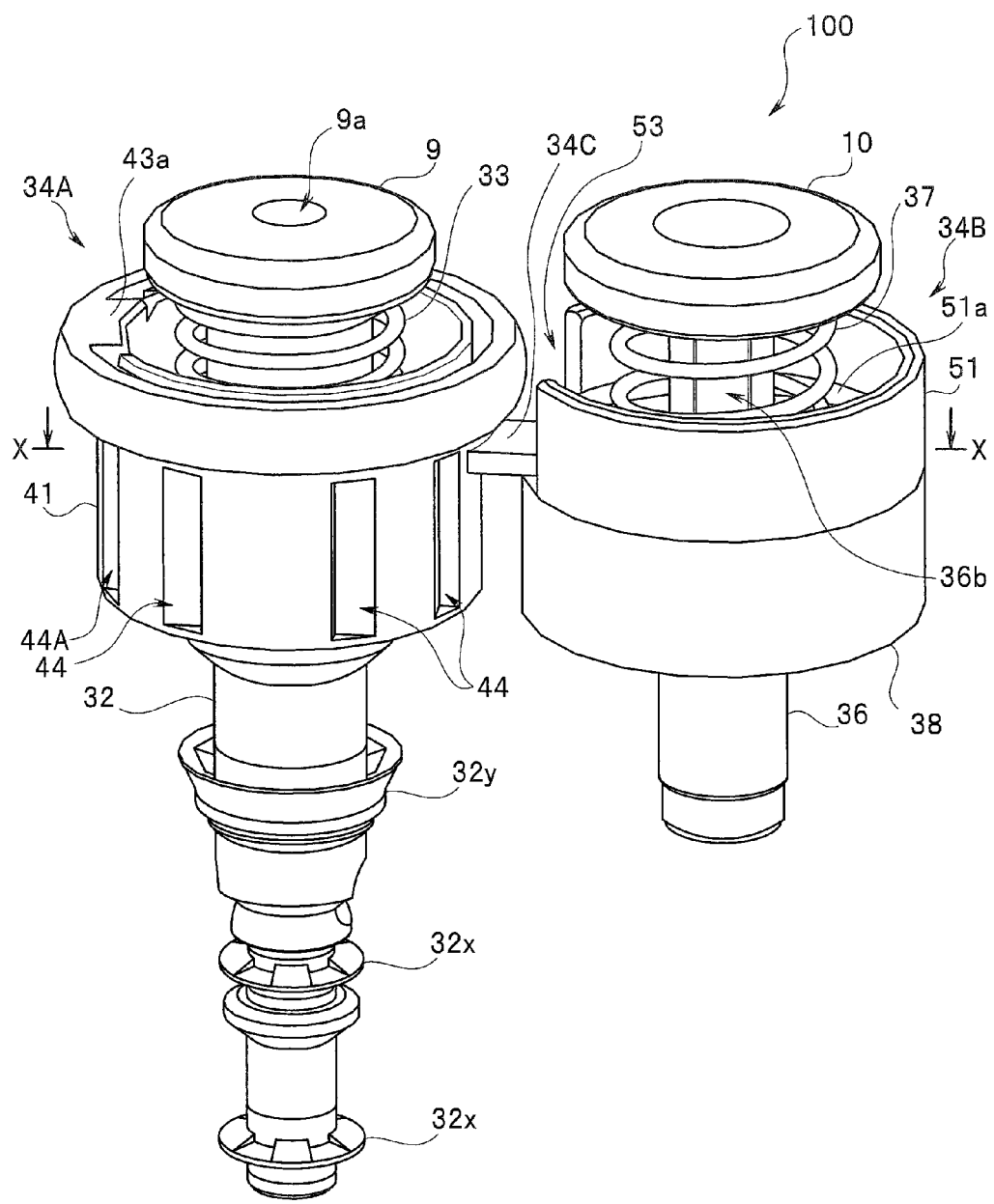
FIG. 5 is a perspective view of the endoscope button unit according to the first embodiment of the present invention.
Figure 6:
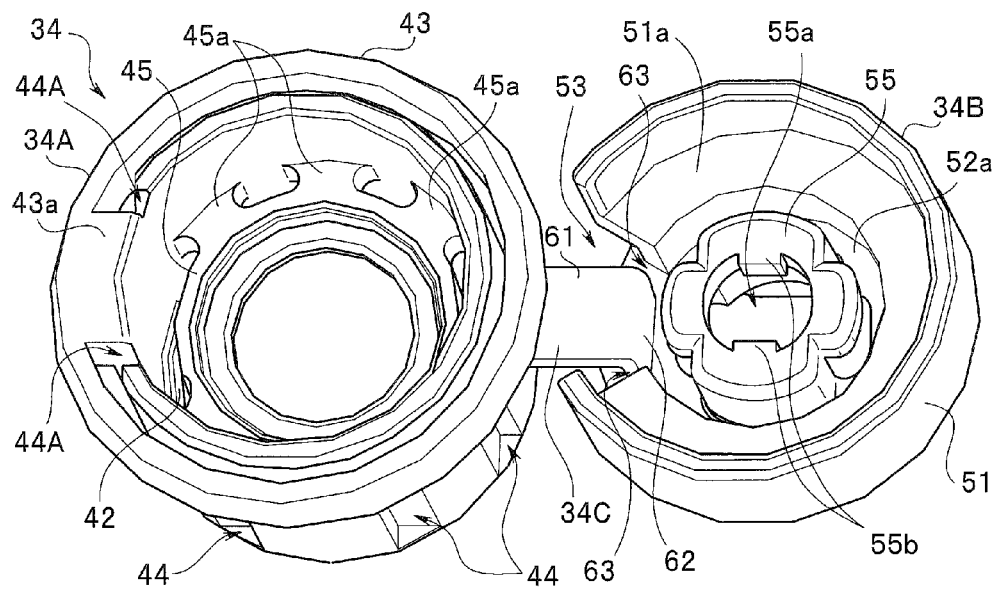
FIG. 6 is a perspective view of a housing 34 seen from a diagonally upper direction, according to the first embodiment of the present invention.
Figure 7:
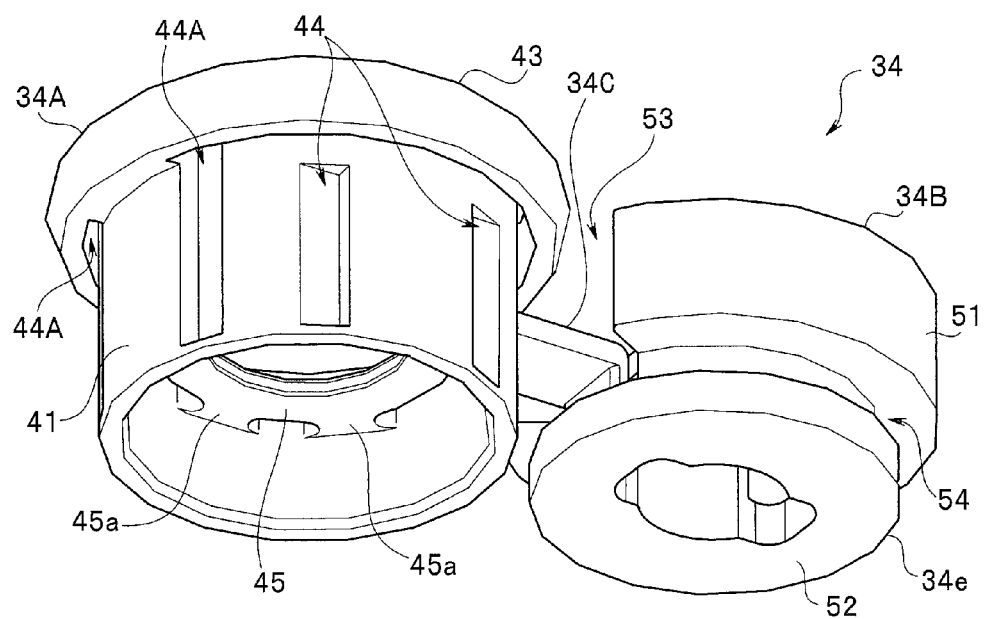
FIG. 7 is a perspective view of the housing 34 seen from a diagonally lower direction, according to the first embodiment of the present invention.
Figure 8:
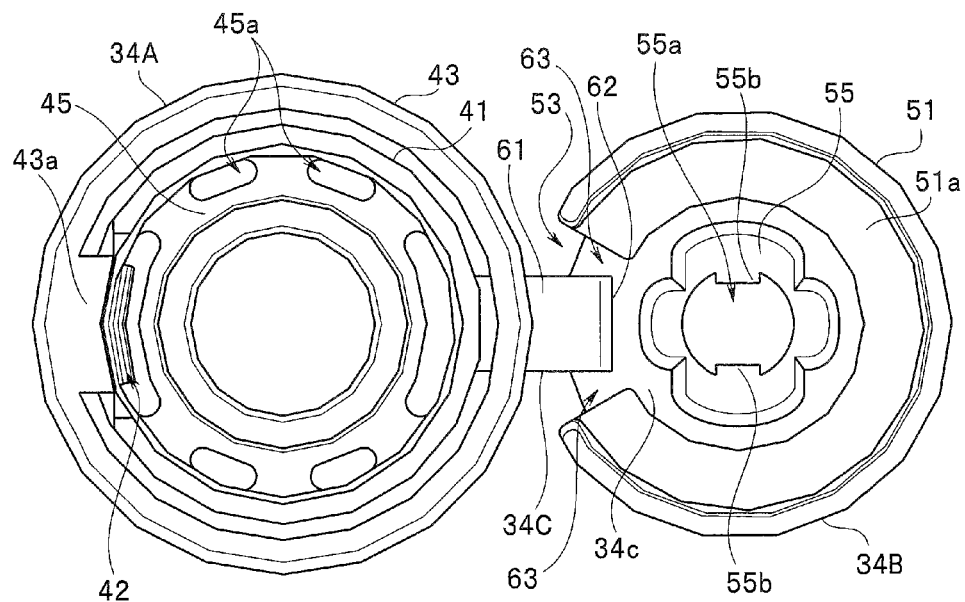
FIG. 8 is a top view of the housing 34 according to the first embodiment of the present invention.
Figure 9:
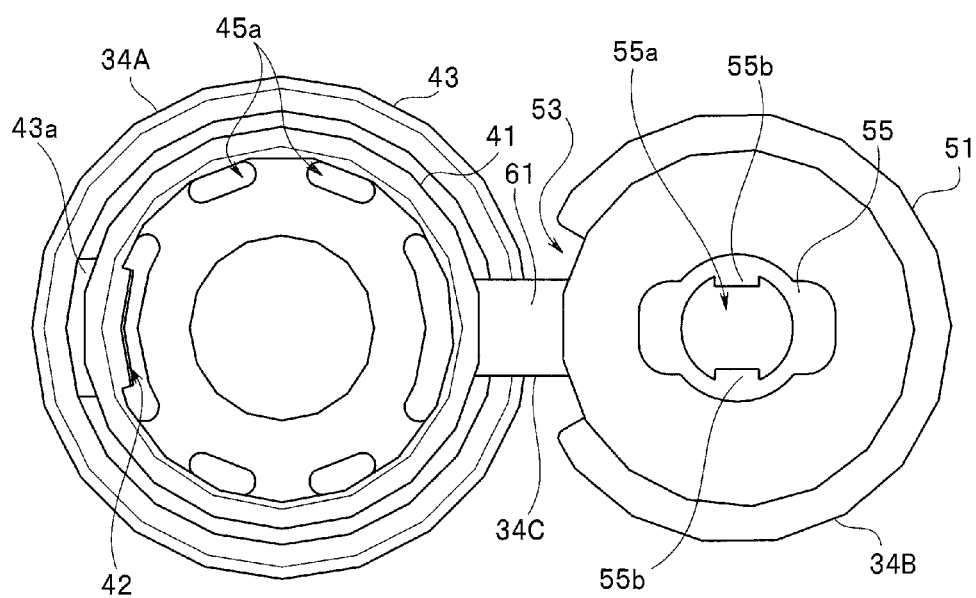
FIG. 9 is a bottom view of the housing 34 according to the first embodiment of the present invention.
Figure 10:
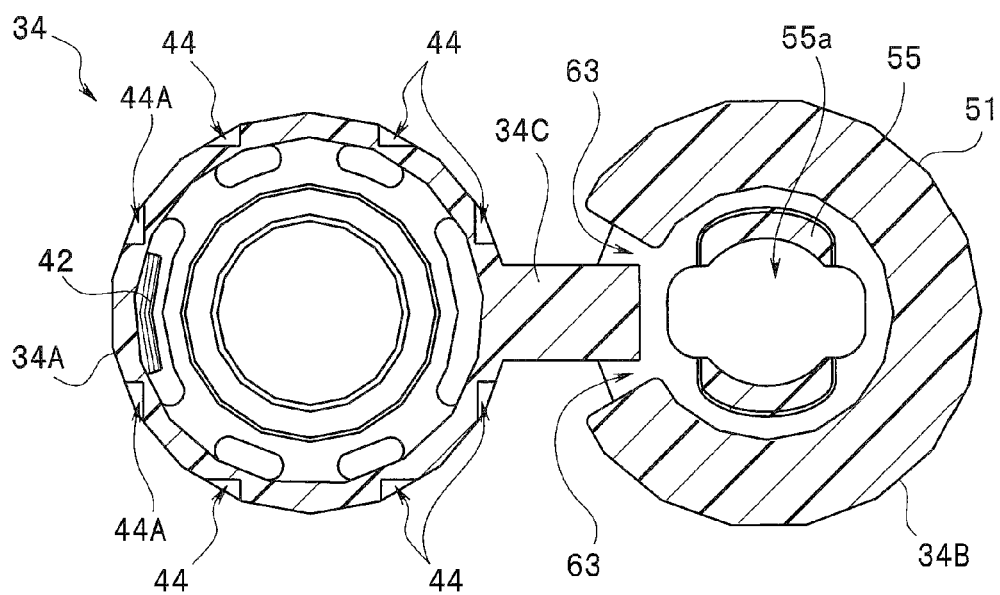
FIG. 10 is a sectional view of the housing 34 along a line X-X in FIG. 5.
Figure 11:
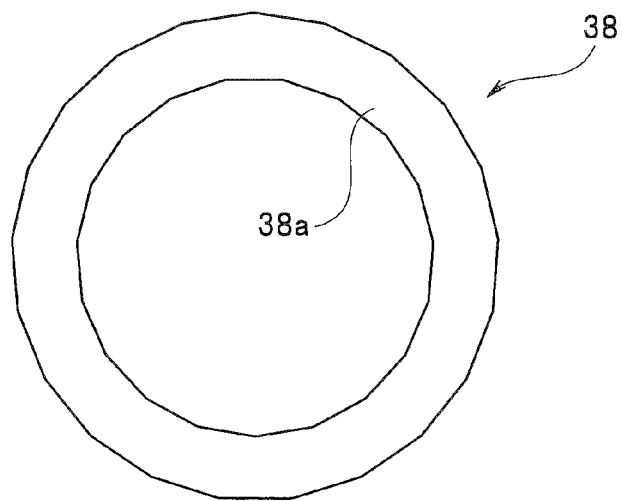
FIG. 11 is a top view of an elastic member 38 according to the first embodiment of the present invention.
Figure 12:
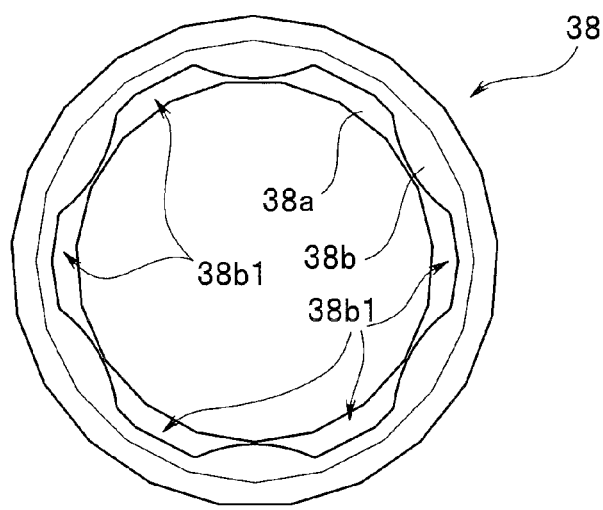
FIG. 12 is a bottom view of the elastic member 38 according to the first embodiment of the present invention.

FIG. 5 is a perspective view of the endoscope button unit 100. FIG. 6 is a perspective view of the housing 34 seen from a diagonally upper direction. FIG. 7 is a perspective view of the housing 34 seen from a diagonally lower direction. FIG. 8 is a top view of the housing 34. FIG. 9 is a bottom view of the housing 34. FIG. 10 is a sectional view of the housing 34 along a line X-X in FIG. 5. FIG. 11 is a top view of the elastic member 38. FIG. 12 is a bottom view of the elastic member 38.

As shown in FIG. 6 and the like, the housing 34 has the two housing portions 34A and 34B, and a connection portion 34C that connects the two housing portions 34A and 34B. The housing 34 is a molded member of a resin, and is formed from polyethylene, for example. That is, the connection portion 34C is a housing connection portion that connects the housing portion 34A and the housing portion 34B. The housing portion 34A, the housing portion 34B and the connection portion 34C are integrally molded.

The housing portion 34A accommodates the air/water feeding valve unit 24, and is fitted to the pipe sleeve 26. The housing portion 34B accommodates the suction valve unit 25, and is fitted to the pipe sleeve 27.

The housing portion 34A has a cylindrical main body portion 41, a claw portion 42 that is provided at a lower portion of the main body portion 41, and a ring-shaped portion 43 that is provided at an upper portion of the main body portion 41. The air/water feeding valve unit 24 is accommodated inside the main body portion 41. The claw portion 42 and the ring-shaped portion 43 are formed by integral molding with the housing portion 34A.

Further, grooves 44 are formed along an axial direction of the cylindrical main body portion 41, on an outer circumferential face of the main body portion 41. The respective grooves 44 are thin-walled portions in which sectional shapes orthogonal to an axial direction of the main body portion 41 have V-shapes.

The claw portion 42 is a convex portion that is formed to protrude inward, on a part of an inner circumferential face of the main body portion 41. The claw portion 42 engages with the outward flange portion 26*b* of the pipe sleeve 26 when the housing portion 34A is fitted to the pipe sleeve 26 (refer to FIG. 2). That is, the claw portion 42 is capable of locking the housing portion 34A to the air/water feeding cylinder 22, and configures a locking portion which is provided in the housing portion 34A.

The ring-shaped portion 43 is a hook portion that is partially raised by a finger of an operator being hooked on the hook portion, as will be described later. That is, the ring-shaped portion 43 is a hook portion that is placed at an upper portion of the housing portion 34A, and can be pulled with use of a finger (or a jig).

In a connection portion 43*a* that is provided from a spot where the claw portion 42 is formed to a spot of an upper portion in the axial direction of the main body portion 41, the ring-shaped portion 43 is connected to the main body portion 41. That is, the connection portion 43*a* is a hook connection portion that connects the housing portion 34A and the ring-shaped portion 43 which is the hook portion.

Two grooves 44A are formed on the outer circumferential face of the main body portion 41, along the axial direction of the main body portion 41 from both sides of the connection portion 43*a*. The respective grooves 44A are also thin-walled portions in which sectional shapes orthogonal to the axial direction of the main body portion 41 have V-shapes.

The plurality of grooves 44 and the two grooves 44A configure thin-walled portions of the main body portion 41.

The plurality of groove-shaped thin-walled portions 44 and 44A are formed on an outer circumferential portion of the main body portion 41. When the main body portion 41 is fitted to the pipe sleeve 26, the thin-walled portions 44 and 44A extend in a circumferential direction, and an inside diameter of the main body portion 41 extends, so that, the main body portion 41 is easily fitted to the pipe sleeve 26.

Further, the two grooves 44A are thin-walled portions of the housing portion 34A, which are formed from a vicinity of the connection portion 43a to the claw portion 42. As will be described later, when the ring-shaped portion 43 is pulled and a part of the housing portion 34A plastically deforms, the two grooves 44A which are the thin-walled portions are broken, whereby locking of the housing portion 34A to the air/water feeding cylinder 22 by the claw portion 42 is released.

The housing portion 34A has a ring-shaped portion 45 that extends inward from the inner circumferential face of the main body portion 41. The ring-shaped portion 45 is connected to an inner wall of the main body portion 41 by a plurality of extended portions 45a that are extended inward from the inner circumferential face of the main body portion 41. A part of a top face of the ring-shaped portion 45 configures the spring reception portion 34b. An undersurface portion of the ring-shaped portion 45 configures the bottom face portion 34a (refer to FIG. 2).

The housing portion 34B has a cylindrical main body portion 51, and an engaging portion 52 that is provided at a lower portion of a bottom face portion 51a of the main body portion 51.

The suction valve unit 25 is accommodated inside the main body portion 51. In a part of an upper portion of the main body portion 51, a cutout portion 53 is formed. The cutout portion 53 is formed in a vicinity of the ring-shaped portion 43 at the housing portion 34A side of the main body portion 51. This is for the purpose of causing a finger to be easily placed on the ring-shaped portion 43 without being hindered by the main body portion 51, when the finger is placed on the ring-shaped portion 43.

A circumferential groove 54 is formed in an outer circumferential portion between the engaging portion 52 and the main body portion 51. An outer circumferential portion of the engaging portion 52 is an outward flange portion at a lower side of the circumferential groove 54.

Further, the engaging portion 52 has an inward flange portion 52a inside (refer to FIG. 2). Inside the main body portion 51, a protruded portion 55 that protrudes to an upper side from a top face of the inward flange portion 52a is included. A hole 55a is formed in a central portion of the protruded portion 55. A top face portion of the inward flange portion 52a configures the spring reception portion 34c.

Two convex portions 55b that protrude inward are formed in the hole 55a. The two convex portions 55b are provided in the hole 55a so that the two convex portions 55 are fitted into the two concave portions 36b which are provided in the piston 36 when the suction valve unit 25 is fitted to the housing portion 34B. When the two convex portions 55b are fitted into the two concave portions 36b, a position of the communication hole 36a1 which is formed in the piston 36 coincides with a position of the opening 30b which is formed in the suction cylinder 23.

An outside diameter of the outward flange portion 34e and an outside diameter of the pipe sleeve 27 are substantially the same (refer to FIG. 2).

The elastic member 38 is a cylindrical member which is formed from a silicone rubber or the like.

As shown in FIG. 2 and FIG. 11, the elastic member 38 is a cylindrical member, and has inward flange portions 38a and 38b at an upper portion and a lower portion respectively.

The inward flange portion 38a has an inside diameter that engages with the circumferential groove 54 of the main body portion 51. The inward flange portion 38b has an inside diameter that engages with a circumferential groove 27c between the two outward flange portions 27a and 27b of the pipe sleeve 27.

In the inward flange portion 38a, an inner side has a shape formed into a circular shape, whereas in the inward flange portion 38b, an inner side is not in a circular shape, but has a plurality of cutout portions 38b1 where parts of a circular shape are cut out.

The connection portion 34C has an L-shape, and has an extended portion 61 that extends toward the protruded portion 55 of the housing portion 34B from the outer circumferential portion of the main body portion 41, and an extended portion 62 that extends toward the spring reception portion 34c of the cutout portion 53 from a distal end portion of the extended portion 61. The extended portion 61 extends in a direction orthogonal to the axis of the main body portion 41 from the outer circumferential portion of the main body portion 41, and the extended portion 62 extends along an axial direction of the main body portion 41. At both sides of the extended portion 62, slits 63 are provided between the extended portion 62 and the main body portion 51. The connection portion 34C has the L-shape, and therefore has flexibility.

That is, the connection portion 34C has the extended portion 62 which is extended along the axial direction of the piston 32, and due to flexibility of the extended portion 62 to the housing portion 34B, the connection portion 34C has flexibility.

When the housing portion 34A is fitted to the pipe sleeve 26, the center axis of the main body portion 41 and a center axis of the pipe sleeve 26 coincide with each other. When the housing portion 34B is fitted to the pipe sleeve 27, a center axis of the main body portion 51 coincides with a center axis of the pipe sleeve 27.

(Operation)

Next, an operation of the endoscope button unit 100 of the present embodiment will be described. First of all, attachment of the housing 34 will be described.

The housing 34 is attached to the pipe sleeves 26 and 27 in a state where the elastic member 38 is attached to the engaging portion 52 of the housing portion 34B, and the air/water feeding valve unit 24 and the suction valve unit 25 are respectively attached to the housing portions 34A and 34B.

The main body portions 41 and 51 are respectively fitted to the pipe sleeves 26 and 27, and due to an error of resin molding of the housing 34, a distance between the center axis of the main body portion 41 and the center axis of the main body portion 51 does not sometimes correspond to a distance between the center axis of the pipe sleeve 26 and the center axis of the pipe sleeve 27 accurately.

However, the connection portion 34C has the L-shape as described above, and the extended portion 62 has flexibility. Consequently, even if an error of resin molding of the housing 34 is present, the extended portion 62 bends to absorb the error, and therefore, the main body portions 41 and 51 can be respectively fitted to the pipe sleeves 26 and 27.

Further, when one of the housing portions 34A and 34B is fitted to one of the two pipe sleeves, and thereafter, the other one of the housing portions 34A and 34B is fitted to the other one of the two pipe sleeves, the extended portion 62 bends, and therefore the operator easily fits the other one of the housing portions 34A and 34B to the other one of the two pipe sleeves.

Further, having the extended portion 62 also provides an effect of absorbing a variation in manufacture or a variation in assembly of a distance between axes of the air/water feeding cylinder 22 and the suction cylinder 23.

Further, if an orientation of the communication hole 36a1 which is formed in the piston 36 deviates with respect to the opening 30b, the suction amount is likely to be reduced, and sucked matters are likely to get stuck. However, in this case, the suction valve unit 25 is only fitted to the housing portion 34B in such a manner that the two convex portions 55b of the hole 55a are fitted into the two concave portions 36b which are provided in the piston 36, whereby the position of the communication hole 36a1 which is formed in the piston 36 and the position of the opening 30b which is formed in the suction cylinder 23 coincide with each other. Consequently, adjustment of the orientation of the piston 36 around the axis at the time of the suction valve unit 25 being fitted to the housing portion 34B is not required.

Conventionally, adjustment of the orientation of the piston has been required so that the orientation of the communication hole 36a1 coincides with the position of the opening 30b when the piston is fitted to the suction cylinder or after the piston is fitted to the suction cylinder. However, if an orientation of the button 10 which is fixed to the piston 36 is matched with the housing portion 34B, adjustment of the orientation of the piston 36 of the suction valve unit 25 is not required when or after the piston 36 is fitted to the suction cylinder 23.

Figure 13:
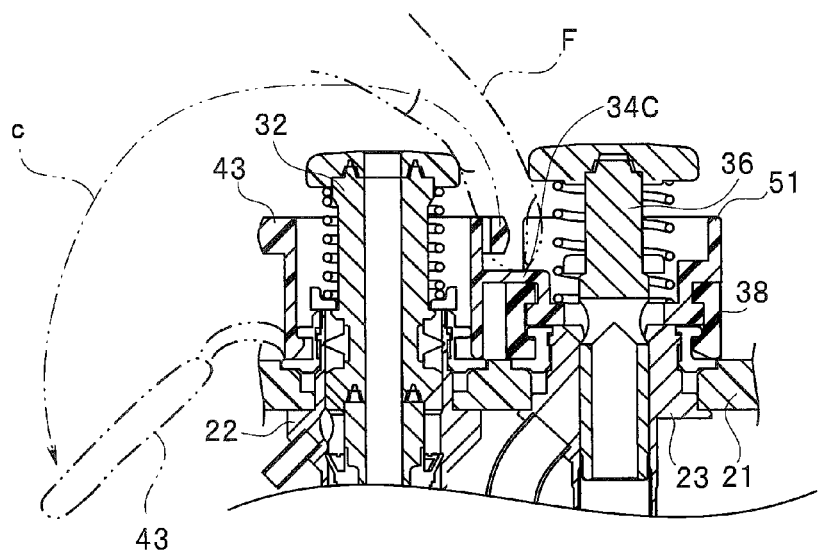
FIG. 13 is a view for explaining detachment of the housing 34, according to the first embodiment of the present invention.
Figure 14:
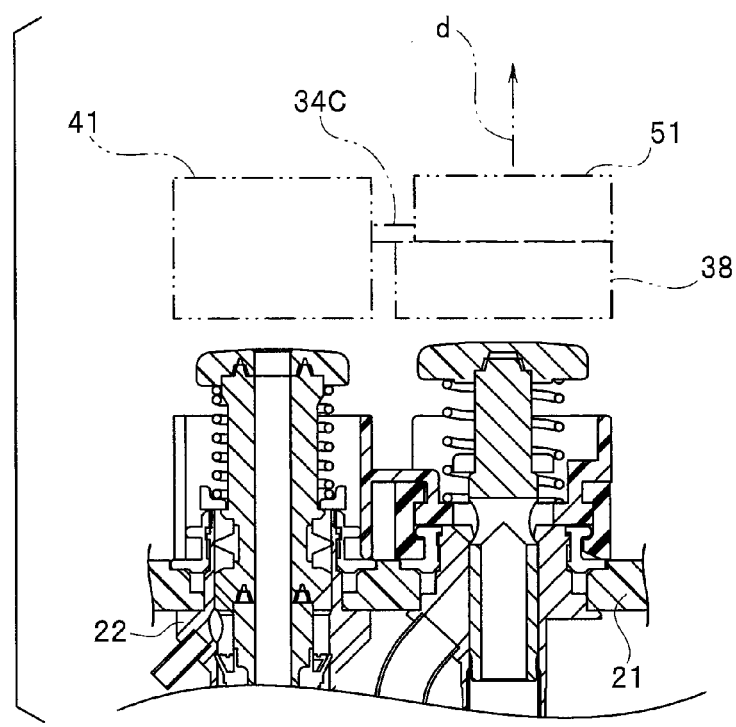
FIG. 14 is a view for explaining detachment of the housing 34, according to the first embodiment of the present invention.

Next, detachment of the housing 34 will be described. FIG. 13 and FIG. 14 are views for explaining detachment of the housing 34.

When the endoscope button unit is detached from the pipe sleeves 26 and 27 after use of the endoscope 1, if the operator hooks a part of the ring-shaped portion 43 at the cutout portion 53 side with a finger F or a jig, and thereafter pulls the connection portion 43a toward the lower side of the main body portion 41, the two grooves 44A of the main body portion 41 are torn off. Since the connection portion 43a is pulled toward the lower portion of the main body portion 41, the ring-shaped portion 43 has the claw portion 42 pulled in the outside diameter direction of the main body portion 41, and as shown in FIG. 13, an engagement state of the claw portion 42 and the outward flange portion 26b of the pipe sleeve 26 is released, so that the ring-shaped portion 43 and the claw portion 42 are separated from the main body portion 41.

More specifically, the grooves 44A which are thin-walled portions are formed in the housing portion 34A from the vicinity of the connection portion 43a to the claw portion 42. When the ring-shaped portion 43 is pulled and a part of the housing portion 34A plastically deforms, the grooves 44A are broken, and engagement of the housing portion 34A to the air/water feeding cylinder 22 by the claw portion 42 is released. Since the main body portion 41 is released from engagement with the pipe sleeve 26, the main body portion 41 can be detached from the pipe sleeve 26. When the housing portion 34A is pulled upward, the housing portion 34B is also pulled up.

The inward flange portion 38a at the upper side of the elastic member 38 engages with the engaging portion 52 of the main body portion 51 in close contact with the engaging portion 52. Since the plurality of cutout portions 38b1 are formed in the inward flange portion 38b at the lower side of the elastic member 38, an engaging force of the inward flange portion 38b and the pipe sleeve 27 is smaller than an engaging force of the inward flange portion 38a and the engaging portion 52.

Consequently, when the housing portion 34B is pulled upward, the main body portion 51 is also pulled upward as shown by an arrow d, so that the elastic member 38 elastically deforms, and engagement of the inward flange portion 38b and the pipe sleeve 27 is released. As a result, the operator can detach the housing portion 34B from the pipe sleeve 27 together with the housing portion 34A, by one operation.

As above, according to the present embodiment, the two housing portions 34A and 34B are connected by the connection portion 34C, and therefore, the operator can detach the two housing portions 34A and 34B respectively including the valve units together from the endoscope.

Further, after the two housing portions 34A and 34B are detached from the endoscope, the housing portion 34A is deformed. Consequently, the operator can easily recognize that the endoscope button unit is already used, and therefore, management for discriminating a used button unit from an unused button unit is not necessary.

Second Embodiment

In the first embodiment, the extended portion 61 of the connection portion 34C extends in the direction orthogonal to the axis of the main body portion 41 from the outer circumferential portion of the main body portion 41, and the extended portion 62 extends along the axial direction (that is, the axial direction of the piston 32) of the main body portion 41, whereas in a second embodiment, the connection portion has an extended portion that connects to a part of the main body portion 41 and a part of the main body portion 51, and extends along the axial direction (that is, the axial direction of the piston 32) of the main body portion 41.

Since an endoscope button unit 100A of the second embodiment has a substantially same configuration as the endoscope button unit 100 of the first embodiment, the same components will be assigned with the same reference signs, explanation of the same components will be omitted, and different components will be described.

Figure 15:
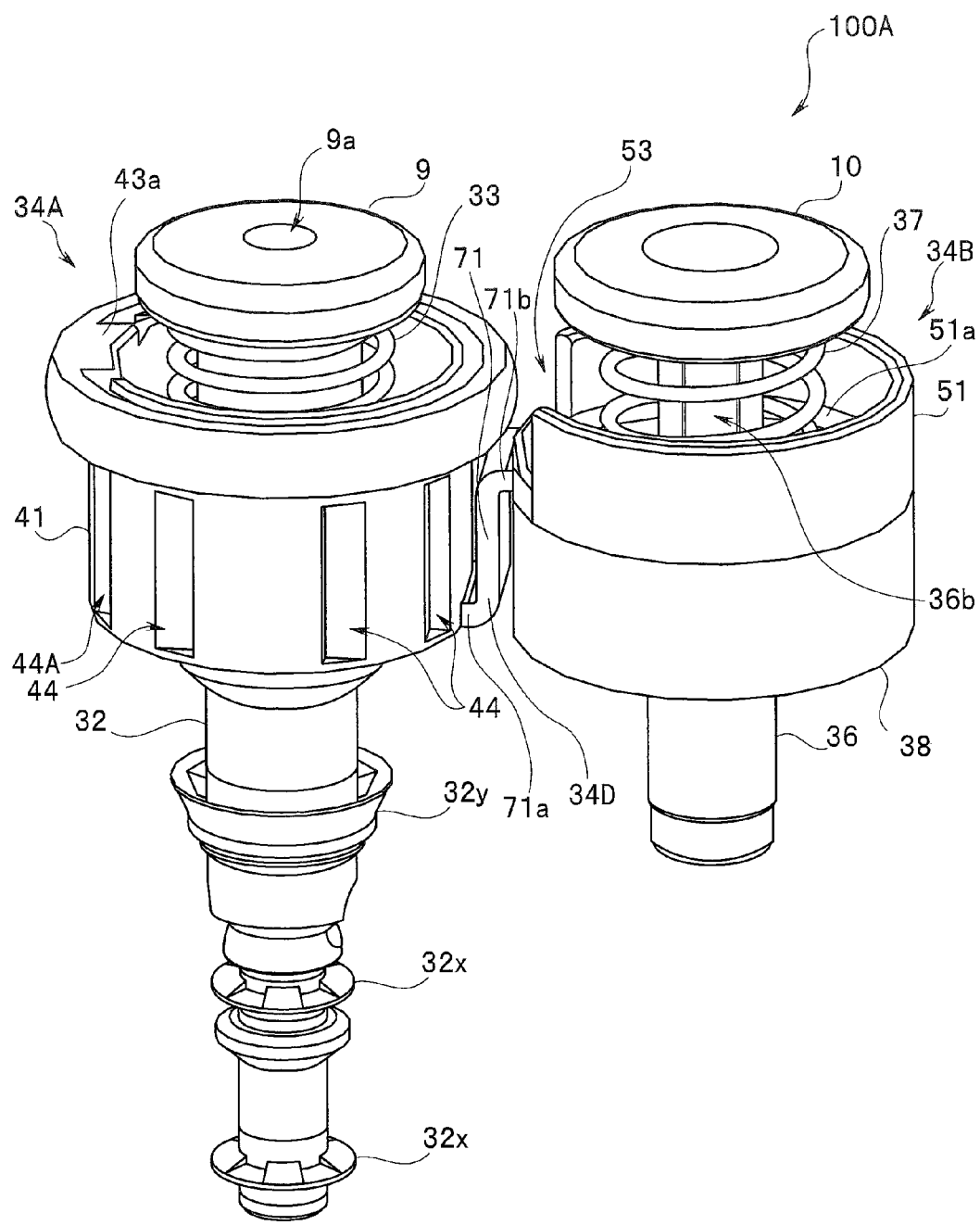
FIG. 15 is a perspective view of an endoscope button unit according to a second embodiment of the present invention.
Figure 16:
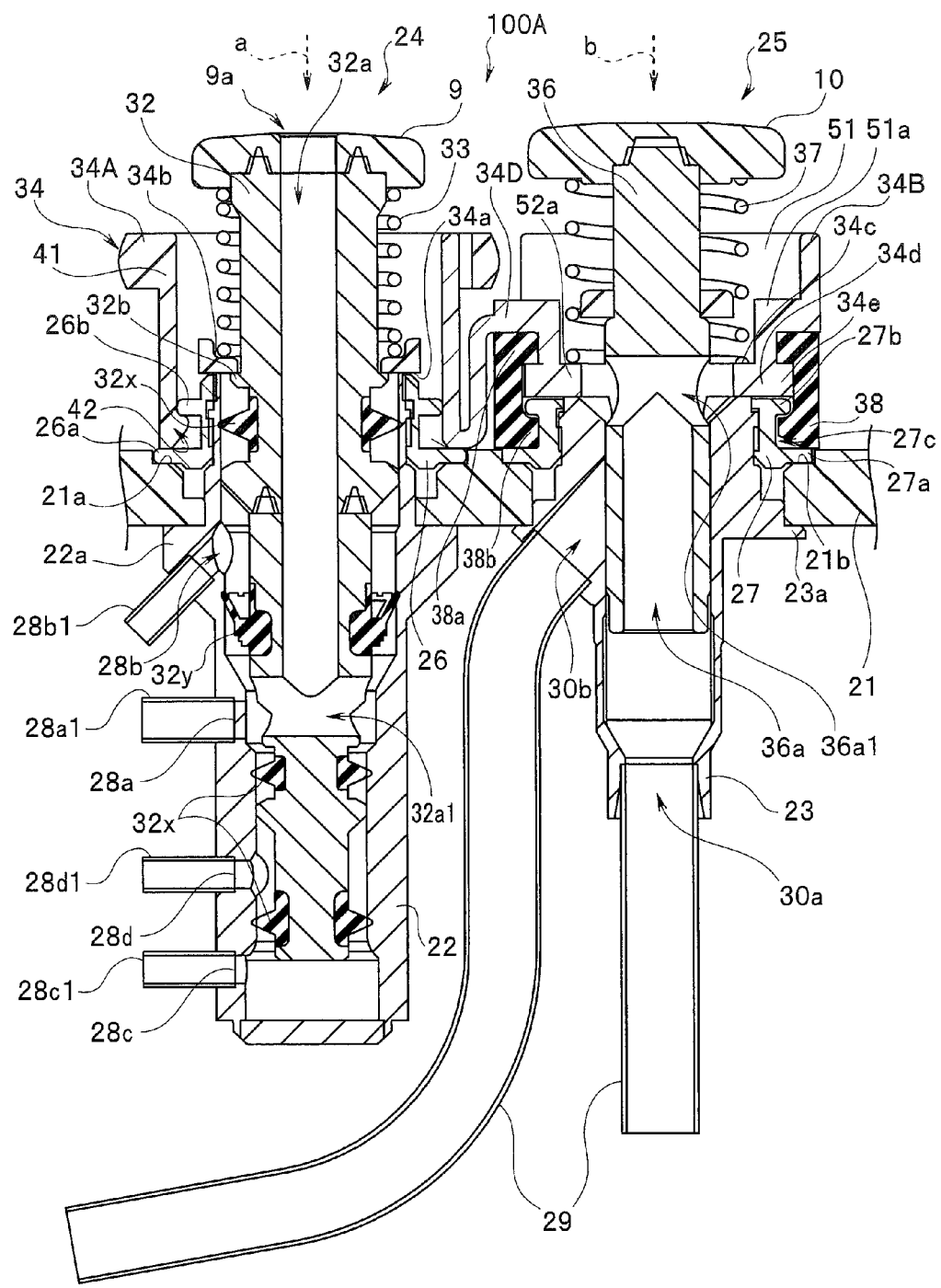
FIG. 16 is a sectional view of the endoscope button unit which is fitted to the air/water feeding cylinder 22 and the suction cylinder 23 which are fixed to the outer sheath member of the operation portion 3, according to the second embodiment of the present invention.
Figure 17:
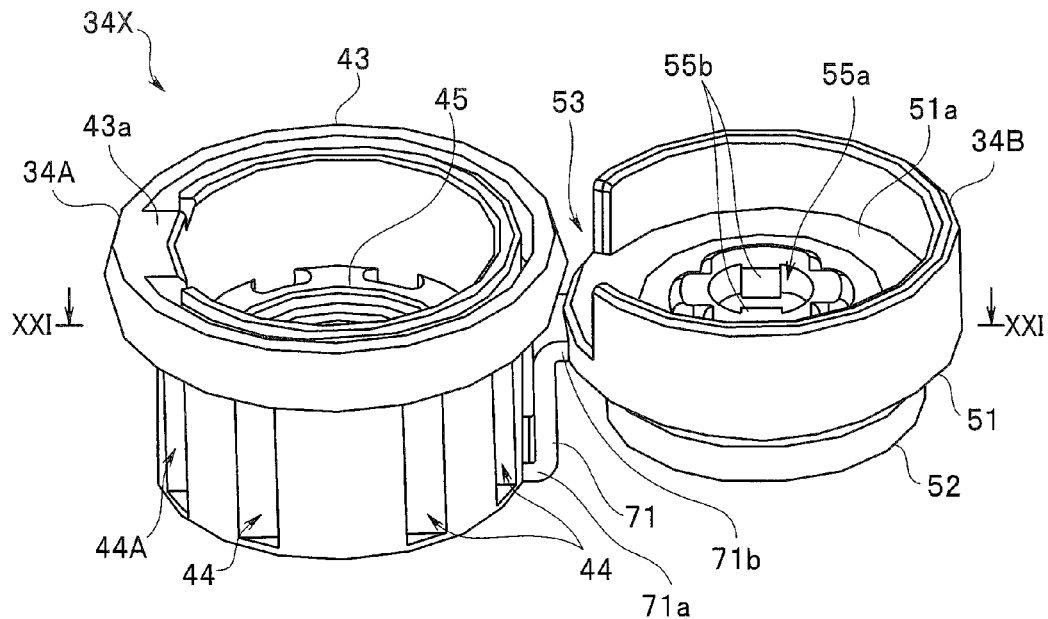
FIG. 17 is a perspective view of a housing 34X seen from a diagonally upper direction, according to the second embodiment of the present invention.
Figure 18:
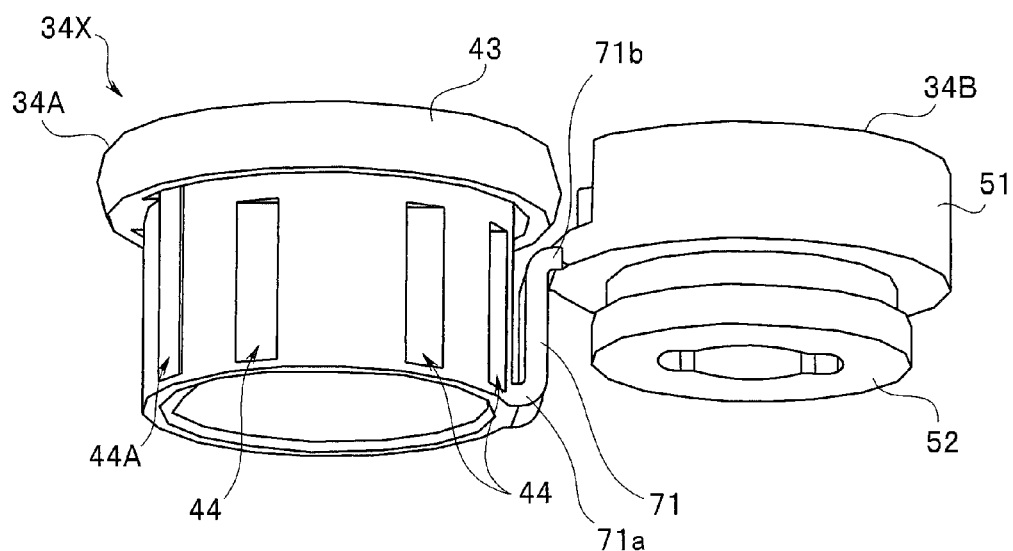
FIG. 18 is a perspective view of the housing 34X seen from a diagonally lower direction, according to the second embodiment of the present invention.
Figure 19:
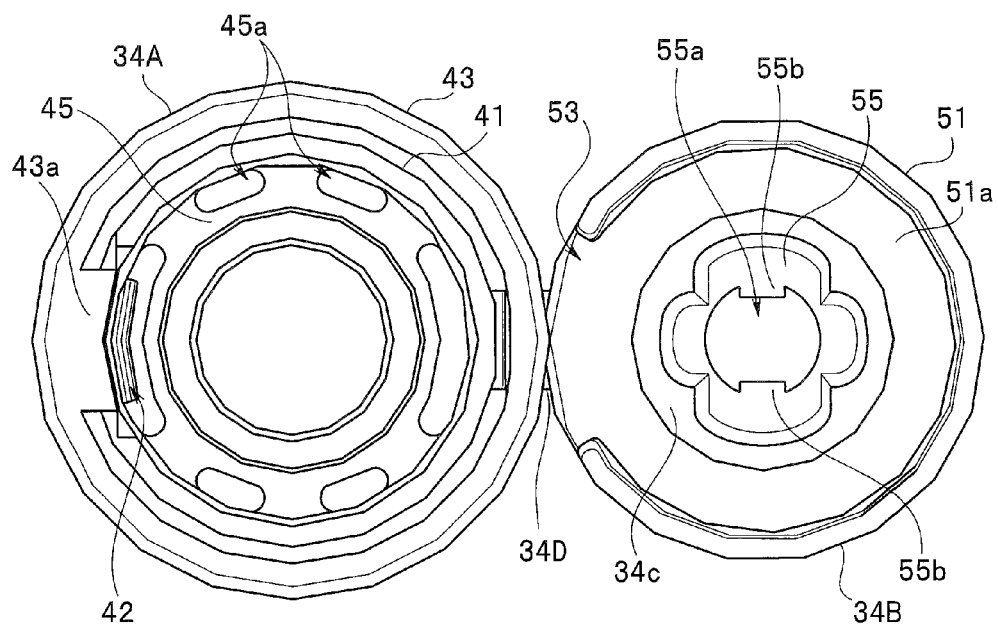
FIG. 19 is a top view of the housing 34X according to the second embodiment of the present invention.
Figure 20:
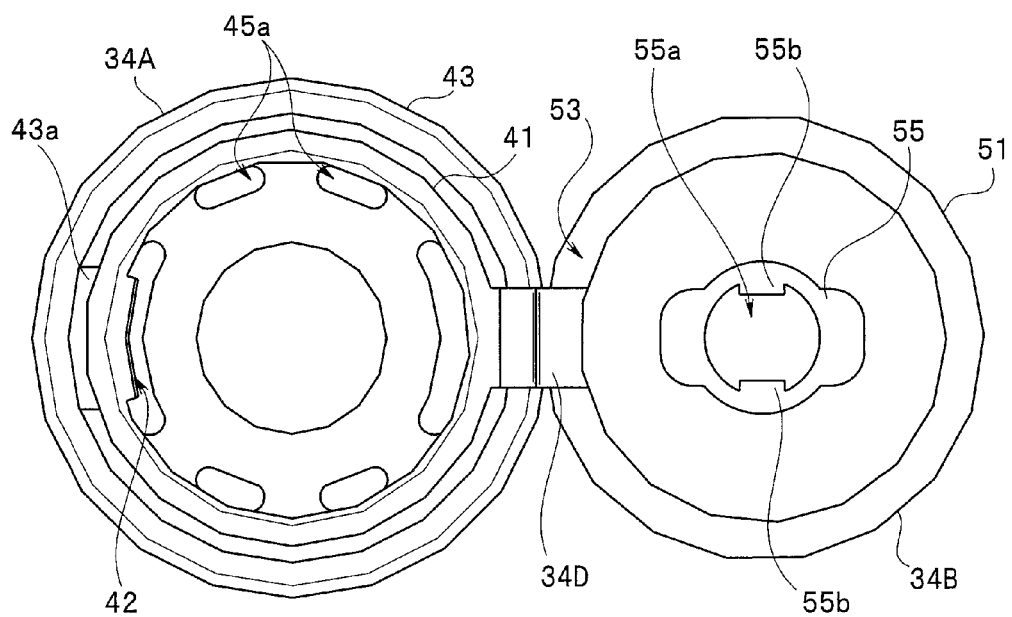
FIG. 20 is a bottom view of the housing 34X according to the second embodiment of the present invention.
Figure 21:
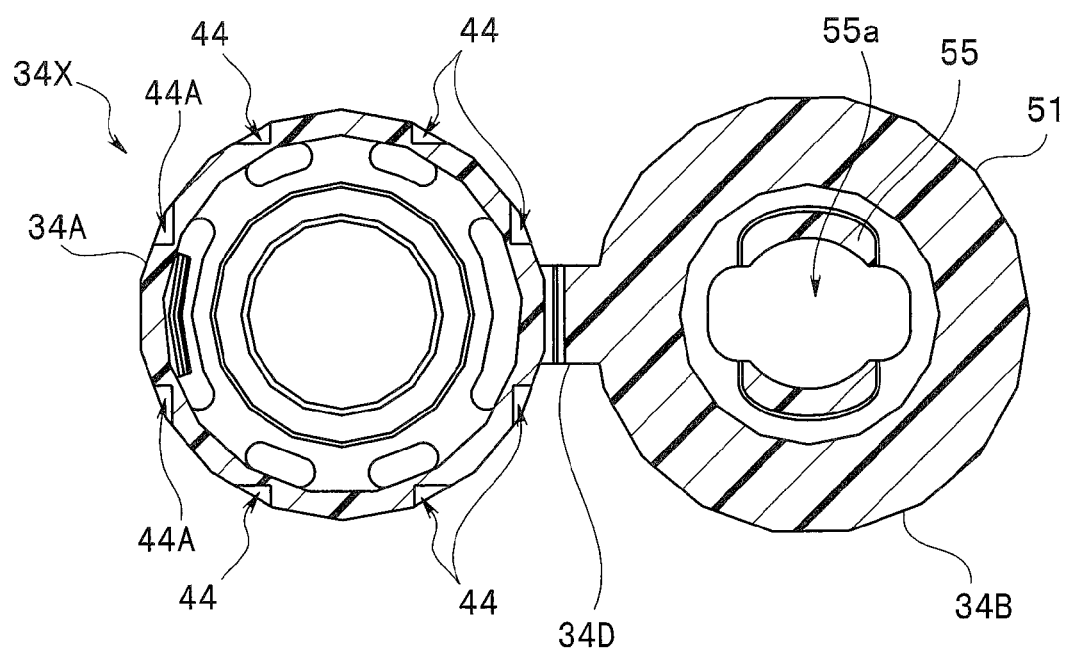
FIG. 21 is a sectional view of the housing 34X along a line XXI-XXI in FIG. 17.

FIG. 15 is a perspective view of the endoscope button unit 100A of the present embodiment. FIG. 16 is a sectional view of the endoscope button unit 100A which is fitted to the air/water feeding cylinder 22 and the suction cylinder 23 which are fixed to the outer sheath member of the operation portion 3. FIG. 17 is a perspective view of a housing 34X seen from a diagonally upper direction. FIG. 18 is a perspective view of the housing 34X seen from a diagonally lower direction. FIG. 19 is a top view of the housing 34X. FIG. 20 is a bottom view of the housing 34X. FIG. 21 is a sectional view of the housing 34X along a line XXI-XXI in FIG. 17.

As shown in FIG. 15 and FIG. 16, a connection portion 34D has a plate-shaped extended portion 71 that extends along the axial direction of the main body portion 41. One end 71a of the extended portion 71 connects to an outer circumferential face at a lower side of the main body portion 41, and the other end 71b of the extended portion 71 connects to the bottom face portion 51a which is protruded to the upper side from the inward flange portion 52a of the main body portion 51.

That is, the connection portion 34D has the extended portion 71 which extends along the axial direction of the piston 32, and the one end 71a of the extended portion 71 is connected to the outer circumferential portion of the housing portion 34A while the other end 71*b* of the extended portion 71 is connected to the outer circumferential portion of the housing portion 34B, whereby the connection portion 34D has flexibility.

Consequently, the endoscope button unit of the present embodiment also has an operation and an effect similar to the operation and the effect of the endoscope button unit of the first embodiment.

Further, in the present embodiment, even if an error is present in a distance between the two housing portions 34A and 34B due to an error in resin molding of the housing 34X, the extended portion 71 bends to absorb the error, as in the housing 34 of the first embodiment, and therefore, the main body portions 41 and 51 can be respectively fitted to the pipe sleeves 26 and 27.

Further, when one of the housing portions 34A and 34B is fitted to one of the two pipe sleeves, and thereafter the other one of the housing portions 34A and 34B is fitted to the other one of the two pipe sleeves, the extended portion 71 bends, and therefore, the other one of the housing portions 34A and 34B is easily fitted to the corresponding other one of the two pipe sleeves.

The above embodiments are described with the button units of the air/water feeding buttons and the suction buttons of the endoscopes for use in the medical field as examples, but the present invention is also applicable to endoscopes in the industrial field without being limited to the medical field, and the button unit is also applicable to other units of buttons without being limited to the units of the air/water feeding button and the suction button.

As above, according to the two embodiments described above, the endoscope button unit and the endoscope with which management for discriminating a used one and an unused one is not required, and at least two valve units can be efficiently detached can be provided.

Further, since the housing portions 34A and 34B in each of the two embodiments can be produced as the single member, reduction in cost of the endoscope is also brought about.

The present invention is not limited to the aforementioned embodiments, and various modifications, alterations and the like can be made within the range without changing the gist of the present invention.

What is claimed is:

1. An endoscope button unit, comprising:
   a first piston capable of being fitted to a first cylinder of an endoscope;
   a first housing portion configured to hold the first piston so that the first piston is capable of advancing and retreating along an axial direction of the first piston;
   a locking portion that is capable of locking the first housing portion to the first cylinder, and is provided at the first housing portion;
   a second piston capable of being fitted to a second cylinder adjacent to the first cylinder of the endoscope;
   a second housing portion configured to hold the second piston so that the second piston is capable of advancing and retreating along an axial direction of the second piston;
   a housing connection portion configured to connect the first housing portion and the second housing portion;
   a hook portion that is placed at an upper portion of the first housing portion and is capable of being pulled;
   a hook connection portion that is provided at the first housing portion at a position opposite to the second housing portion with respect to an axis of the first piston of the first housing portion, the hook connection portion being configured to connect the first housing portion and the hook portion;
   a cutout portion that is formed at the second housing portion at a position facing the first housing portion; and
   a thin-walled portion formed at the first housing portion from a vicinity of the hook connection portion to the locking portion,
   wherein when the hook portion is pulled and a part of the first housing portion elastically deforms, the thin-walled portion is broken, and the locking of the first housing portion to the first cylinder by the locking portion is released.

2. The endoscope button unit according to claim 1, wherein the first housing portion, the second housing portion, and the housing connection portion are integrally molded together.

3. The endoscope button unit according to claim 1, wherein the locking portion is molded integrally with the first housing portion.

4. The endoscope button unit according to claim 1, wherein the housing connection portion has flexibility.

5. The endoscope button unit according to claim 4,
   wherein the housing connection portion has an extended portion that extends along the axial direction of the first piston, and
   by flexibility of the extended portion to the second housing portion, the housing connection portion has flexibility.

6. The endoscope button unit according to claim 4,
   wherein the housing connection portion has an extended portion that extends along the axial direction of the first piston, and
   one end of the extended portion is connected to an outer circumferential portion of the first housing portion, and another end of the extended portion is connected to an outer circumferential portion of the second housing portion, whereby the housing connection portion has flexibility.

7. The endoscope button unit according to claim 1, wherein the first housing portion is made of a resin.

8. The endoscope button unit according to claim 1, wherein the second housing portion is made of a resin.

9. The endoscope button unit according to claim 1, wherein the hook portion is capable of being pulled by a finger or a jig.

10. The endoscope button unit according to claim 1, wherein the hook portion is in a ring shape.

11. The endoscope button unit according to claim 1, wherein the second housing portion is fitted to the second cylinder by an elastic member.

12. An endoscope having an endoscope button unit fitted to the endoscope, and a first cylinder and a second cylinder that are fixed to an outer sheath member of the endoscope, the endoscope button unit comprising:
   a first piston capable of being fitted to the first cylinder;
   a first housing portion configured to hold the first piston so that the first piston is capable of advancing and retreating along an axial direction of the first piston;
   a locking portion that is capable of locking the first housing portion to the first cylinder, and is provided at the first housing portion;
   a second piston capable of being fitted to the second cylinder adjacent to the first cylinder of the endoscope;

a second housing portion configured to hold the second piston so that the second piston is capable of advancing and retreating along an axial direction of the second piston;
a housing connection portion configured to connect the first housing portion and the second housing portion;
a hook portion that is placed at an upper portion of the first housing portion and is capable of being pulled;
a hook connection portion that is provided at the first housing portion at a position opposite to the second housing portion with respect to an axis of the first piston of the first housing portion, the hook connection portion being configured to connect the first housing portion and the hook portion;
a cutout portion that is formed at the second housing portion at a position facing the first housing portion; and
a thin-walled portion formed at the first housing portion from a vicinity of the hook connection portion to the locking portion,
wherein when the hook portion is pulled and a part of the first housing portion elastically deforms, the thin-walled portion is broken, and the locking of the first housing portion to the first cylinder by the locking portion is released.

* * * * *